(12) United States Patent
Nagai

(10) Patent No.: US 9,213,108 B2
(45) Date of Patent: Dec. 15, 2015

(54) PHOTON COUNTING TYPE IMAGE DETECTOR, X-RAY DIAGNOSIS APPARATUS AND X-RAY COMPUTED TOMOGRAPHY APPARATUS

(71) Applicants: Kabushiki Kaisha Toshiba, Minato-ku (JP); Toshiba Medical Systems Corporation, Otawara-shi (JP)

(72) Inventor: Seiichirou Nagai, Otawara (JP)

(73) Assignees: KABUSHIKI KAISHA TOSHIBA, Minato-ku (JP); TOSHIBA MEDICAL SYSTEMS CORPORATION, Otawara-shi (JP)

(*) Notice: Subject to any disclaimer, the term of this patent is extended or adjusted under 35 U.S.C. 154(b) by 279 days.

(21) Appl. No.: 13/924,131

(22) Filed: Jun. 21, 2013

(65) Prior Publication Data

US 2013/0287175 A1 Oct. 31, 2013

Related U.S. Application Data

(63) Continuation of application No. PCT/JP2012/067396, filed on Jul. 6, 2012.

(30) Foreign Application Priority Data

Jul. 7, 2011 (JP) .................................. 2011-151158

(51) Int. Cl.
*A61B 6/00* (2006.01)
*G01T 1/17* (2006.01)
(Continued)

(52) U.S. Cl.
CPC ................. *G01T 1/17* (2013.01); *A61B 6/4233* (2013.01); *A61B 6/4241* (2013.01); *G01T 1/247* (2013.01); *H04N 5/32* (2013.01); *A61B 6/025* (2013.01); *A61B 6/0414* (2013.01); *A61B 6/502* (2013.01)

(58) Field of Classification Search
CPC ...................................................... A61B 6/4241
See application file for complete search history.

(56) References Cited

U.S. PATENT DOCUMENTS 4,651,005 A 3/1987 Baba et al.
6,281,504 B1 8/2001 Takayama et al.
(Continued)

FOREIGN PATENT DOCUMENTS

JP 60-080746 A 5/1985
JP 63-171387 A 7/1988
(Continued)

OTHER PUBLICATIONS

Extended European Search Report issued Mar. 6, 2015 in Patent Application No. 12807377.2.
(Continued)

*Primary Examiner* — Hoon Song
(74) *Attorney, Agent, or Firm* — Oblon, McClelland, Maier & Neustadt, L.L.P.

(57) ABSTRACT

A photon counting type image detector has: a semiconductor cell that detects an X-ray photon; a charge amplifier that generates a plurality of electric pulses each being based on an electric charge collected in response to the detected X-ray photon; a comparator that discriminates a peak value of each of the electric pulses; a threshold logic circuit that performs control so as to count none of the peak-discriminated electric pulses corresponding to energy of characteristic X-rays produced in the semiconductor cell; and a counter that counts the discriminated electric pulses as controlled by the threshold logic circuit.

13 Claims, 12 Drawing Sheets

(51) Int. Cl.
*G01T 1/24* (2006.01)
*H04N 5/32* (2006.01)
*A61B 6/02* (2006.01)
*A61B 6/04* (2006.01)

(56) References Cited

U.S. PATENT DOCUMENTS

| | | |
|---|---|---|
| 6,714,621 B2 | 3/2004 | Rick et al. |
| 7,496,176 B2 | 2/2009 | Aslund |
| 7,595,492 B2 | 9/2009 | Nakamura et al. |
| 7,696,483 B2 | 4/2010 | Tkaczyk et al. |
| 7,947,956 B2 | 5/2011 | Nakamura et al. |
| 8,213,566 B2 | 7/2012 | Roessl et al. |
| 2008/0099689 A1 | 5/2008 | Nygard et al. |
| 2008/0260094 A1* | 10/2008 | Carmi ............... 378/19 |
| 2010/0025593 A1 | 2/2010 | Proksa |
| 2010/0232568 A1 | 9/2010 | Heismann et al. |
| 2011/0012014 A1* | 1/2011 | Livne et al. ........ 250/252.1 |
| 2014/0105370 A1* | 4/2014 | Yamakawa et al. .......... 378/207 |

FOREIGN PATENT DOCUMENTS

| | | |
|---|---|---|
| JP | 11-352233 A | 12/1999 |
| JP | 2000-023961 A | 1/2000 |
| JP | 2000-189409 A | 7/2000 |
| JP | 2002-119501 A | 4/2002 |
| JP | 2003-210442 A | 7/2003 |
| JP | 2006-101926 A | 4/2006 |
| JP | 2007-007407 A | 1/2007 |
| JP | 2007-155360 A | 6/2007 |
| JP | 2008-272093 A | 11/2008 |
| JP | 2011-89901 A | 5/2011 |
| WO | 2006/68130 A1 | 6/2006 |
| WO | 2008/044439 A1 | 4/2008 |
| WO | WO 2008/093275 A2 | 8/2008 |
| WO | 2010/004460 A1 | 1/2010 |

OTHER PUBLICATIONS

D. Pennicard et al., "Simulated Performance of High-Z Detectors with Medipix3 Readout", Journal of Instrumentation, vol. 6, No. 6, XP020206128, Jun. 13, 2011, 27 pages.

Cheng Xu et al., "Evaluation of Energy Loss and Charge Sharing in Cadmium Telluride Detectors for Photon-Counting Computed Tomography", IEEE Transactions on Nuclear Science, vol. 58, No. 3, XP011477452, Jun. 1, 2011, 12 pages.

International Search Report mailed Oct. 9, 2012 for PCT/JP2012/067396 filed on Jul. 6, 2012 with English Translation.

Takayuki Ishida, New Medical Radiology and Radiological Technology Diagnostic Imaging Instruments, 1st edition, Ishiyaku Publishers, Inc., Hideho Ohata, Jul. 25, 2010, pp. 196 to 199, Chapter 2 Iyo Gazo eno Oyo, the 3rd edition Gazo Shori to Igaku eno Oyo, 7 Mammography.

International Preliminary Report on Patentability and Written Opinion issued Jan. 7, 2014 in PCT/JP2012/067396 (submitting English translation only).

* cited by examiner

|   | A | B | C | D | E |
|---|---|---|---|---|---|
| 1 | Ek<br>Ek−El<br>El | Ek<br>Ek−El<br>El | Ek<br>Ek−El<br>El | Ek<br>Ek−El<br>El | Ek<br>Ek−El<br>El |
| 2 | Ek<br>Ek−El<br>El | Ek<br>Ek−El<br>El | Ek<br>Ek−El<br>El | Ek<br>Ek−El<br>El | Ek<br>Ek−El<br>El |
| 3 | Ek<br>Ek−El<br>El | Ek<br>Ek−El<br>El | Ein :m1<br>Ein−Ek :m2<br>Ein−Ek+El :m3 | Ek<br>Ek−El<br>El | Ek<br>Ek−El<br>El |
| 4 | Ek<br>Ek−El<br>El | Ek<br>Ek−El<br>El | Ek<br>Ek−El<br>El | Ek<br>Ek−El<br>El | Ek<br>Ek−El<br>El |
| 5 | Ek<br>Ek−El<br>El | Ek<br>Ek−El<br>El | Ek<br>Ek−El<br>El | Ek<br>Ek−El<br>El | Ek<br>Ek−El<br>El |

FIG. 7

| | COMPARATOR 534 | COMPARATOR 533 | COMPARATOR 532 | COMPARATOR 531 | LOGIC OF THRESHOLD LOGIC CIRCUIT 55 | | | |
|---|---|---|---|---|---|---|---|---|
| | >TH4 (THL) | >TH3 | >TH2 | >TH1 (THH) | 534·(!533) | 533·(!532)·(!531) | 532·(!531) | 531 |
| LOW ENERGY NOISE | 0 | 0 | 0 | 0 | 0 | 0 | 0 | 0 |
| (INCIDENT X-RAY ENERGY)−(CHARACTERISTIC X-RAY ENERGY) | 1 | 0 | 0 | 0 | 1 | 0 | 0 | 0 |
| CHARACTERISTIC X-RAY ENERGY | 1 | 1 | 0 | 0 | 0 | 1 | 0 | 0 |
| INCIDENT X-RAY ENERGY | 1 | 1 | 1 | 0 | 0 | 0 | 1 | 0 |
| HIGH ENERGY NOISE | 1 | 1 | 1 | 1 | 0 | 0 | 0 | 1 |

FIG. 9

PHOTON COUNTING TYPE IMAGE DETECTOR, X-RAY DIAGNOSIS APPARATUS AND X-RAY COMPUTED TOMOGRAPHY APPARATUS

CROSS-REFERENCE TO RELATED APPLICATION

This application is a Continuation Application of No. PCT/JP2012/067396, filed on Jul. 6 2012, and the PCT application is based upon and claims the benefit of priority from Japanese Patent Application No. 2011-151158, filed on Jul. 7, 2011, the entire contents of which are incorporated herein by reference.

FIELD

The embodiment relates to a photon counting type image detector counting an X-ray photon (particle), and an X-ray diagnosis apparatus and an X-ray computed tomography apparatus having the photon counting type image detector.

BACKGROUND

A photon counting type image detector having a semiconductor cell (X-ray detecting material) and a plurality of processing circuits formed by an ASIC layer is used for an X-ray diagnosis apparatus and an X-ray computed tomography apparatus. If X-ray photons each having energy Ein as many as an integer N are absorbed by a certain pixel, it is desirable in an ideal operation of the photon counting type image detector that a signal detected by an incident pixel of the X-ray photons be proportional to Ein times N and that signals on pixels surrounding the incident pixel of the X-ray photons be zero.

According to ordinary technologies, though, as signal leakage into surrounding pixels occurs in a process for detecting X-rays, the signal on the incident pixel of the X-ray photons is not proportional to Ein times N in practice, and a signal on a pixel around the incident pixel of the X-ray photons is not zero.

The fact that a signal appears on a nearby pixel which is different from the incident pixel of the X-ray photons means that space resolution is degraded in image characteristics.

Further, the process in which a signal leaks into a nearby pixel is a stochastic process. Thus, if a plurality of X-ray photons arrives at a certain pixel, results of signal leakage are not the same each time of incidence. This contributes to generating noise on an image in image characteristics.

BRIEF DESCRIPTION OF THE DRAWINGS

In accompanying drawings,

FIGS. 3A-3E are diagrams each showing an example of energy absorbed by the photon counting type image detector in a case where one X-ray photon arrives at a certain pixel included in the photon counting type image detector according to the present embodiment;

FIG. 7 is a diagram showing an example of energy absorbed by the photon counting type image detector in a case where X-ray photons arrive at a certain pixel included in the photon counting type image detector according to the present embodiment;

FIG. 9 is a diagram illustrating logical operation for counting none of characteristic X-ray energy by using comparators of four stages;

DETAILED DESCRIPTION

A photon counting type image detector, an X-ray diagnosis apparatus and an X-ray computed tomography apparatus according to the present embodiment is described with reference to the attached drawings.

To solve the above-described problems, the present embodiments provide the photon counting type image detector including: an X-ray detecting material configured to detect an X-ray photon; a charge-to-voltage converter configured to generate a plurality of electric pulses each being based on an electric charge collected in response to the detected X-ray photon; an energy discriminating unit configured to discriminate a peak value of each of the electric pulses; a controller configured to perform control so as to count none of the peak-discriminated electric pulses corresponding to energy of characteristic X-rays produced in the X-ray detecting material; and a counting unit configured to count the discriminated electric pulses as controlled by the controller.

The photon counting type image detector according to the embodiment is what an X-ray diagnosis apparatus and an X-ray computed tomography apparatus, etc., is equipped with, and will be explained below as what a mammography apparatus being one of X-ray diagnosis apparatus is equipped with.

Figure 1:
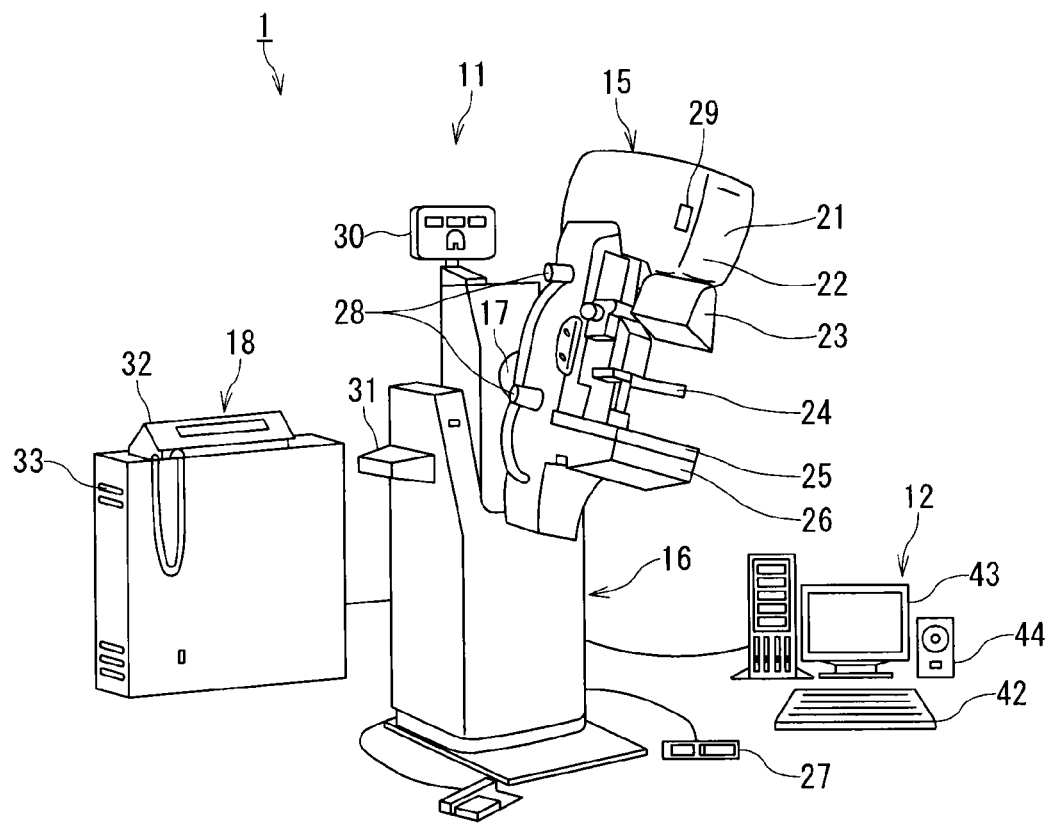
FIG. 1 is a diagrammatic perspective view showing an external structure of the whole mammography apparatus according to the present embodiment.

FIG. 1 is a diagrammatic perspective view showing an external structure of the whole mammography apparatus according to the present embodiment.

FIG. 1 shows the mammography apparatus 1 according the embodiment which photographs a breast (subject) of a patient. The mammography apparatus 1 is formed by an imaging system 11 and an imaging control/image processing system 12.

The imaging system 11 has an arm section 15, a stand section 16, a joint section 17 and an operation section 18. The arm section 15 is pivotally supported by the stand section 16 so as to rotate via and around the joint section 17.

The arm section 15 has an X-ray tube 21, an X-ray beam quality adjustment filter/irradiation field limiting mask 22, a faceguard 23, a pressure board 24, an anti-scatter grid 25, a photon counting type image detector 26, a pressure foot pedal 27, a C-arm up and down/rotation fine adjustment switch 28 and an alarm lamp 29. The stand section 16 has an information display panel 30 and a side panel 31. The operation section 18 has an imaging condition setting panel 32 and a high voltage supply device 33.

The X-ray tube 21 of the arm section 15 is a vacuum tube to be supplied with high voltage power by the high voltage supply device 33 in the operation panel 18 for radiating X-rays toward the photon counting type image detector 26 via a breast of a patient according to conditions of the high voltage power.

The X-ray beam quality adjustment filter/irradiation field limiting mask 22 is arranged in front of the X-ray tube 21. The X-ray beam quality adjustment filter/irradiation field limiting mask 22 is an adjustment tool for adjusting a quality of X-rays produced by the X-ray tube 21 and limiting an irradiation field.

The faceguard 23 is a protection tool for protecting the head of the patient from exposure to X-rays in time of imaging.

The pressure board 24 is a pressure tool to be provided above the photon counting type image detector 26 so as to press the breast of the patient against the photon counting type image detector 26. The pressure board 24 is formed by transparent resin and is movably supported in contact with and separate from the photon counting type image detector 26. Then, the arm section 15 can press the breast of the patient by moving the pressure board 24 towards the photon counting type image detector 26 so as to make the breast substantially evenly thin. The pressure board 24 moves up and down by being driven by a driving mechanism (not shown) formed by a motor for moving the pressure board 24 up and down if an operator such as an engineer, etc., operates the pressure foot pedal 27.

The anti-scatter grid 25 is a tool for removing scattered radiation so as to improve contrast of an image.

The photon counting type image detector 26 has a semiconductor cell (X-ray detecting material) S and a plurality of processing circuits C formed by an ASIC layer AS described later. The photon counting type image detector 26 outputs a digital signal which is provided to the imaging control/image processing system 12.

The pressure foot pedal 27 is a pedal that the operator steps on so as to adjust the position of the pressure board 24 in an up and down direction.

The C-arm up and down/rotation fine adjustment switch 28 is a switch for moving up and down or rotating a C-arm formed by the X-ray tube 21, the photon counting type image detector 26, etc.

As the alarm lamp 29, an LED (light emitting diode), an LCD (liquid crystal display), etc., are enumerated. The alarm lamp 29 is lit or blinks as controlled by the imaging control/image processing system 12.

The information display panel 30 of the stand section 16 is a panel for displaying various kinds of information such as pressure information, etc.

The side panel 31 is an operation panel for controlling the respective portions of the mammography apparatus 1.

The imaging condition setting panel 32 in the operation section 18 is a panel for setting conditions for X-ray imaging.

The high voltage supply device 33 is a device for supplying the X-ray tube 21 in the arm section 15 with voltage.

If the X-ray tube 21 of the imaging system 11 produces X-rays, the X-ray beam quality adjustment filter/irradiation field limiting mask 22 limits a range to be irradiated with the X-rays. Then, the X-rays are radiated towards the breast pressed between the pressure board 24 and the photon counting type image detector 26. Then, the X-rays having passed through the breast are detected by the photon counting type image detector 26, and are outputted to the imaging control/image processing system 12 as a digital signal.

The imaging control/image processing system 12 is a system which entirely controls the mammography apparatus 1 and performs image processing regarding an image obtained by the imaging system 11, etc. The imaging control/image processing system 12 includes an input device 42, a display device 43, a speaker 44, etc.

Figure 2:
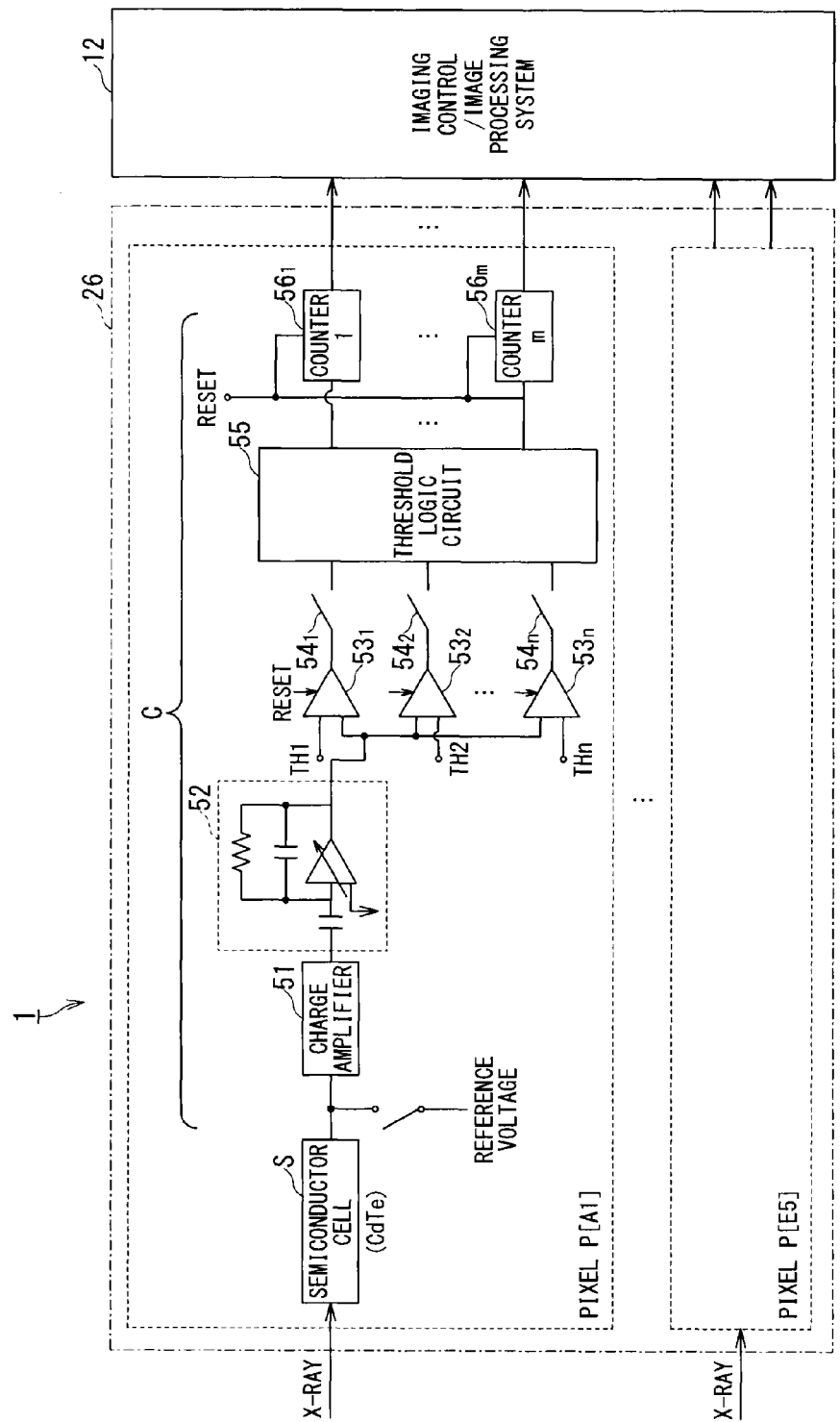
FIG. 2 is an electric block diagram centered around the photon counting type image detector according to the present embodiment.

FIG. 2 is an electric block diagram centered around the photon counting type image detector 26 according to the present embodiment.

As shown in FIG. 2, the photon counting type image detector 26 has a semiconductor cell S for every pixel P and a processing circuit C formed by an ASIC layer AS for every pixel P. It is supposed for explanation here, as shown in FIGS. 3A through 3E, that the photon counting type image detector 26 has 25 pixels Ps from a pixel P[A1] on A-th row and first channel to a pixel P[E5] on E-th row and 5-th channel.

The processing circuits C each have a charge amplifier 51, a waveform shaping circuit 52, comparators (Dual Discri) $53_1$-$53_n$ of n stages (n is a positive integer), switches $54_1$-$54_n$ of n stages, a threshold logic circuit (Discri Logic) 55 and counters (Counter CLK) $56_1$-$56_m$ of m stages.

The charge amplifier 51 is coupled with each of plural collecting electrodes of the semiconductor cell S. The charge amplifier 51 outputs electric charges collected in response to an incident X-ray particle as a voltage pulse signal. An output end of the charge amplifier 51 is coupled with the waveform shaping circuit 52 whose gain and offset can be adjusted.

The waveform shaping circuit 52 processes a waveform of a detected voltage pulse signal according to a gain and an offset adjusted beforehand for waveform shaping. The gain and the offset of the waveform shaping circuit 52 are adjustment parameters for which unevenness of charge-up characteristics for electric charges of respective collective pixels of the semiconductor cell S is taken into account. If the gain and the offset of the waveform shaping circuit 52 are adjusted beforehand for every pixel by calibration work, waveform shaping having excluded such unevenness can be done. As a result, a waveform-shaped pulse signal outputted by the waveform shaping circuit 52 of each of collection channels substantially has a characteristic on which an amount of energy of the incident X-ray particle is reflected, and such unevenness among the pixels is substantially solved. An output end of the waveform shaping circuit 52 is coupled with a compared input end of each of the plural comparators $53_1$-$53_n$.

Reference values TH1 (upper limit reference value THH) through THn (lower limit reference value THL) which are different from one another are each applied to reference input ends of the comparators $53_1$-$53_n$, respectively. A peak value of one pulse signal (energy of the absorbed X-ray photon) coming from the waveform shaping circuit 52 is compared with the reference values TH1-THn which are different from one another so that the energy of the X-ray photon (X-ray particle) absorbed by the semiconductor cell S can be classified into one of plural energy regions which are separated and set beforehand. If n equals three, e.g., the energy region into which the X-ray energy is classified differs depending upon which of the reference values TH1-TH3 the peak value of the pulse signal is over. If the peak value is between the reference values TH1 and TH2, the energy of the absorbed X-ray photon is classified so as to be included in a first energy region. If the peak value is between the reference values TH2 and TH3, the energy of the absorbed X-ray photon is classified so as to be included in a second energy region. If the peak value is equal to or lower than the reference value TH3 (lower limit reference value THL) or equal to or higher than the reference value TH1 (upper limit reference value THH), the X-ray energy is classified in such a way that a disturbance or white noise coming from the semiconductor cell S or the charge amplifier 51 is prevented from being detected. The case where the peak value is equal to or higher than the reference value TH1 (upper limit reference value THH) may occur as well if two or more X-ray photons arrive at the pixel at the same time. Such an event is considered here to improbably occur, though, and is treated as not relating to a main signal forming image information similarly as a disturbance.

Incidentally, the number of the reference values, i.e., the number of the energy regions which are able to be discriminated from one another is not limited to three. The number of the reference values may be two, four, etc., or may be one depending upon circumstances. If the number of the reference values is one, only information regarding whether an X-ray photon has arrived is obtained. The output ends of the comparators $53_1$-$53_n$ are connected with the switches $54_1$-$54_n$, respectively.

The switches $54_1$-$54_n$ are designed to be each turned on if a pulse signal outputted from a corresponding one of the comparators $53_1$-$53_n$ is over a corresponding one of the reference values TH1-THn of the switches $54_1$-$54_n$, respectively, and to be each turned off otherwise. The switch $54_1$, e.g., is designed to be turned on if a pulse signal outputted from the comparator $53_1$ is over the reference value TH1 of the switch $54_1$, and to be turned off otherwise. The output ends of the switches $54_1$-$54_n$ are each connected with the threshold logic circuit 55.

The threshold logic circuit 55 checks which of the comparators $53_1$-$53_n$ are on (off) on the basis of pulse signals outputted individually by the switches $54_1$-$54_n$, and produces a clock pulse signal so as to count output pulses corresponding to a largest pulse signal of one of the comparators $53_1$-$53_n$ being on. Plural output ends of the threshold logic circuit 55 are each coupled with each of plural counters $56_1$-$56_m$ and the clock pulses are counted. The plural counters $56_1$-$56_m$ each work in such a way as to count correspondingly to the peak value of the pulse signal. A pulse being over TH2 and smaller than TH1, e.g., is counted by the counter $56_1$, and a pulse being over TH3 and smaller than TH2 is counted by the counter $56_2$ (similarly hereinafter). In this case, the number m of necessary counters is written as m=n−1 by the use of the number n of the comparators.

The number m of the counters is sometimes m<n−1, as another example, by the use of the number n of the comparators. That corresponds to a case where the number of the pulses having been peak-discriminated by the respective comparators is counted not in each of peak value ranges but in gathered plural peak value ranges. The smallest number m of the counters is m=1. As the clock pulses outputted by the threshold logic circuit 55 is counted by one counter in this case, the counter counts the number of the photons without energy discriminating the energy of the X-ray photons.

The counters $56_1$-$56_m$ each count the clock pulses outputted by the threshold logic circuit 55 up and measure the number of X-ray photons classified into the energy region that the relevant counter is in charge of for a certain period of time.

The photon counting type image detector 26 counts the number of the X-ray photons having arrived at the respective pixels Ps of the photon counting type image detector 26 in this way by means of the plural counters $56_1$-$56_m$ in each of the energy regions which correspond to the number m of the stages of the counters for a certain period of time until being reset. Resultant counted values, i.e., counted numbers of the X-ray photons are read from the plural counters $56_1$-$56_m$ as detected data (raw data) of digital quantities. The data is read for every pixel P in the ASIC layer AS.

The counted value data of each of the pixels P[A1]-P[E5] is individually sent to the imaging control/image processing system 12.

FIGS. 3A-3E are diagrams each showing an example of energy absorbed by the photon counting type image detector 26 in a case where one X-ray photon arrives at a certain pixel P included in the photon counting type image detector 26 according to the present embodiment. As detection of radiation is based on stochastic interaction between the radiation and detecting material in general, the radiation may pass through without interaction unless a layer of the detecting material is thick enough. Suppose that the semiconductor cell S in the photon counting type image detector 26 is thick enough, and that substantially 100 percent of the X-ray photons having arrived perform interaction to give energy into the semiconductor cell S.

FIG. 3A illustrates energy absorbed by the photon counting type image detector 26 in a case where one X-ray photon of energy Ein arrives at a pixel P[C3] on the C-th row and third channel included in the pixels Ps which form the photon counting type image detector 26, and the total energy Ein of the X-ray photon is absorbed by the incident pixel P[C3]. FIG. 3B illustrates energy absorbed by the photon counting type image detector 26 in a case where one X-ray photon of energy Ein arrives at the pixel P[C3], and total energy Ek of K X-ray caused by a photoelectric effect having occurred on the incident pixel P[C3] is absorbed by a non-incident pixel P[C2] excepting the incident pixel P[C3]. FIG. 3C illustrates energy absorbed by the photon counting type image detector 26 in a case where one X-ray photon of energy Ein arrives at the pixel P[C3], and K X-ray of energy Ek caused by a photoelectric effect having occurred on the incident pixel P[C3] run out of a detecting membrane. FIG. 3D illustrates energy absorbed by the photon counting type image detector 26 in a case where one X-ray photon of energy Ein arrives at the pixel P[C3], and K X-ray of energy Ek caused by a photoelectric effect having occurred on the incident pixel P[C3] causes a photoelectric effect on a non-incident pixel P[C2] and total energy El of produced L X-ray is absorbed by a non-incident pixel P[D1] excepting the non-incident pixel P[C2]. FIG. 3E illustrates energy absorbed by the photon counting type image detector 26 in a case where one X-ray photon of energy Ein arrives at the pixel P[C3], and K X-ray of energy Ek caused by a photoelectric effect having occurred on the incident pixel P[C3] causes a photoelectric effect on a non-incident pixel P[C2] and total energy of produced L X-ray is absorbed by the incident pixel P[C3].

As a process in which X-rays are absorbed by detecting membrane is a stochastic process and thus any one of the examples shown in FIGS. 3B-3E may occur, energy is absorbed by a non-incident pixel P excepting the incident pixel P[C3] as well in an exemplary case where one X-ray photon arrives at the pixel P[C3], resulting in degraded resolution of the X-ray image. Further, as energy stored in the pixel P[C3] is not constant in the respective examples shown in FIGS. 3B-3E and a non-incident pixel P which absorbs energy is not fixed, image noise is caused in the X-ray image.

Figure 4A:
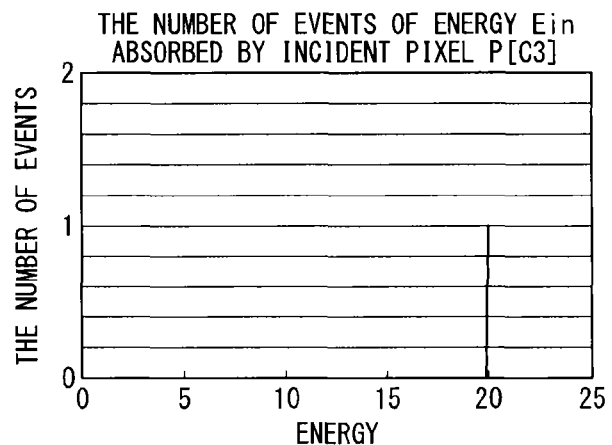
FIGS. 4A-4C are diagrams each showing, in a case where one X-ray photon arrives at a certain pixel included in the photon counting type image detector according to the present embodiment, the number of events of energy absorbed by the incident pixel.
Figure 4B:
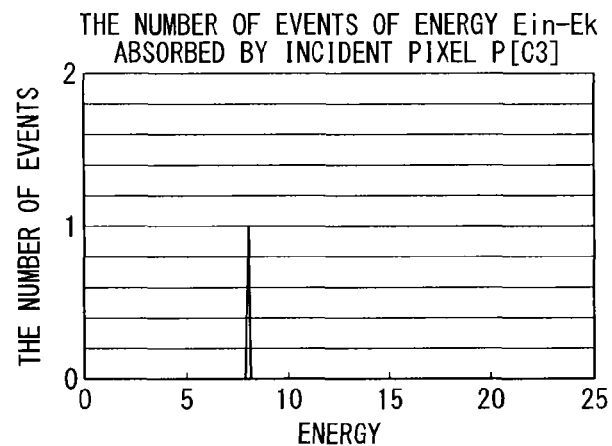
Figure 4C:
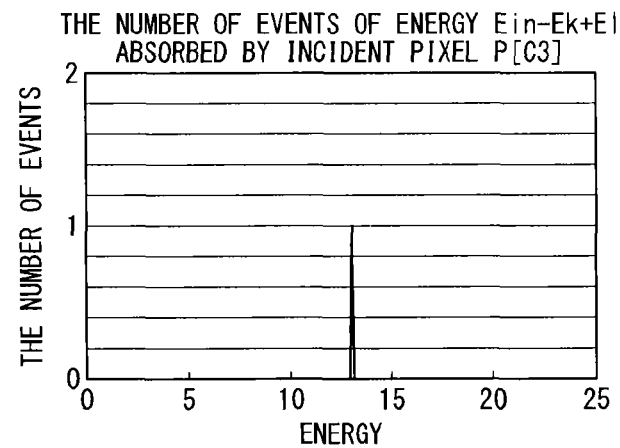

FIGS. 4A-4C are diagrams each showing, in a case where one X-ray photon arrives at a certain pixel P included in the photon counting type image detector 26 according to the present embodiment, the number of events of energy absorbed by the incident pixel P. Incidentally, let the energy Ein, Ek and El be "20", "12" and "5", respectively, in FIGS. 4A-4C.

FIG. 4A shows the number of events of the energy Ein absorbed by the incident pixel P[C3] counted by the counters $56_1$-$56_m$ in the incident pixel P[C3] shown in FIG. 3A. FIG. 4B shows the number of events of energy Ein-Ek absorbed by the incident pixel P[C3] counted by the counters $56_1$-$56_m$ in the incident pixel P[C3] shown in FIGS. 3B-3D. FIG. 4C shows the number of events of energy Ein-Ek+El absorbed by the incident pixel P[C3] counted by the counters $56_1$-$56_m$ in the incident pixel P[C3] shown in FIG. 3E. It is supposed in FIGS. 4A-4C and FIGS. 5A-5C described later that the number n of the stages of the comparators and the number m of the stages of the counters are large enough, and that incident X-ray energy can be discriminated from characteristic X-ray energy.

Figure 5A:
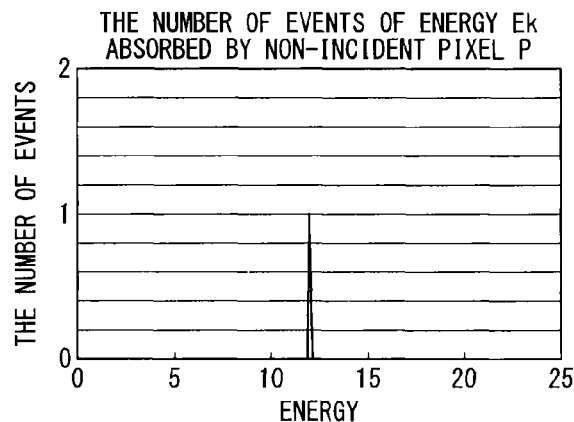
FIGS. 5A-5C are diagrams each showing, in a case where one X-ray photon arrives at a certain pixel included in the photon counting type image detector according to the present embodiment, the number of events of energy absorbed by a non-incident pixel.
Figure 5B:
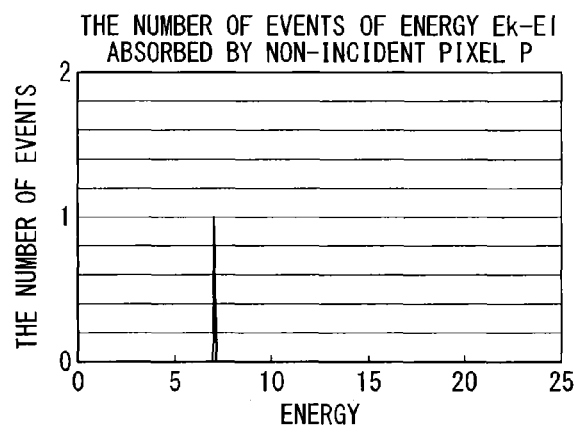
Figure 5C:
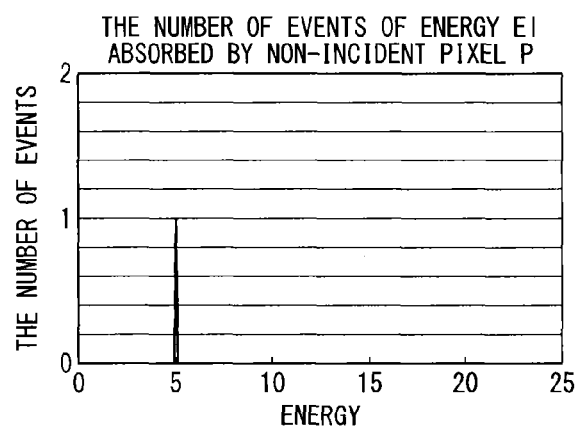

FIGS. 5A-5C are diagrams each showing, in a case where one X-ray photon arrives at a certain pixel P included in the photon counting type image detector 26 according to the present embodiment, the number of events of energy absorbed by a non-incident pixel P. Incidentally, let the energy Ein, Ek and El be "20", "12" and "5", respectively, in FIGS. 5A-5C similarly as in FIGS. 4A-4C.

FIG. 5A shows the number of events of the energy Ek absorbed by the non-incident pixel P[C2] counted by the counters $56_1$-$56_m$ in the non-incident pixel P[C2] shown in FIG. 3B. FIG. 5B shows the number of events of energy Ek-El absorbed by the non-incident pixel P[C2] counted by the counters $56_1$-$56_m$ in the non-incident pixel P[C2] shown in FIGS. 3D and 3E. FIG. 5C shows the number of events of the energy El absorbed by the non-incident pixel P[D1] counted by the counters $56_1$-$56_m$ in the non-incident pixel P[D1] shown in FIG. 3D.

Figure 6A:
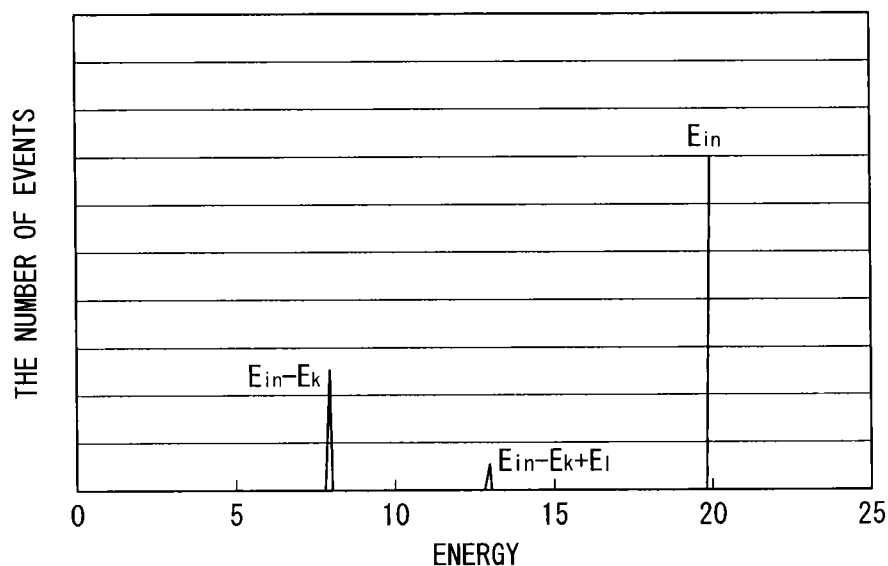
FIGS. 6A and 6B are diagrams each showing, in a case where a plurality of X-ray photons arrives at a certain pixel included in the photon counting type image detector according to the present embodiment, an exemplary energy spectrum on the photon counting type image detector.
Figure 6B:
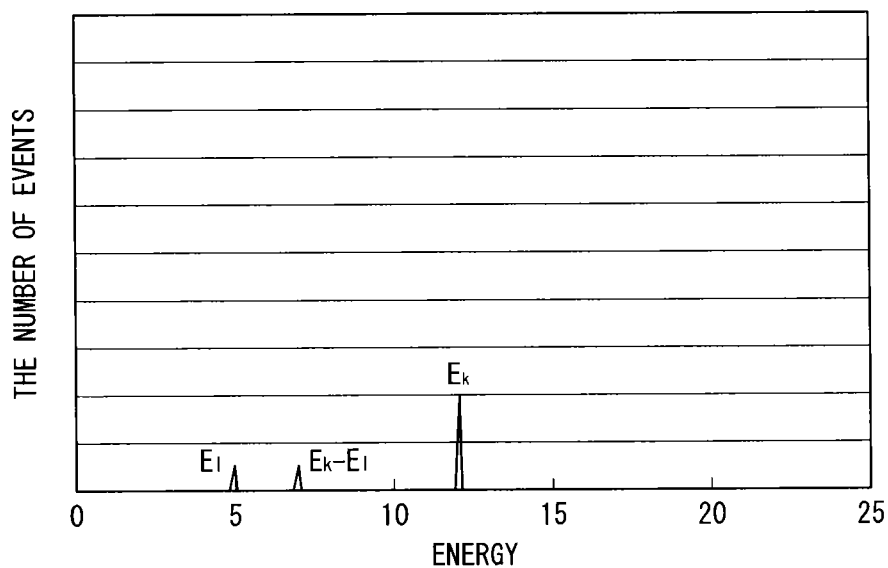

FIGS. 6A and 6B are diagrams each showing, in a case where a plurality of X-ray photons arrives at a certain pixel P included in the photon counting type image detector 26 according to the present embodiment, an exemplary energy spectrum on the photon counting type image detector 26. Incidentally, let the energy Ein, Ek and El be "20", "12" and "5", respectively, in FIGS. 6A and 6B similarly as in FIGS. 4A-4C and 5A-5C.

FIG. 6A shows, in a case where a plurality of X-ray photons of energy Ein individually arrive at the pixel P[C3], an energy spectrum on the incident pixel P[C3]. FIG. 6B shows, in a case where a plurality of X-ray photons of energy Ein individually arrive at the pixel P[C3], an energy spectrum on the non-incident pixel P.

If a plurality of X-ray photons arrives at the pixel P[C3], one of phenomena explained by the use of FIGS. 3A-3E occurs with a certain probability distribution each time the X-ray photons arrive, and these are accumulated on the photon counting type image detector 26 for a period of time for X-ray radiation. In the photon counting type image detector 26 in which a function to detect an X-ray photon and to discriminate its absorbed energy is formed in each of the pixels Ps, the energy spectrum shown in FIG. 6A based on FIGS. 4A-4C is obtained on the incident pixel P[C3] of the X-ray photons, and the energy spectrum shown in FIG. 6B based on FIGS. 5A-5C is obtained on the non-incident pixel P of the X-ray photons. Incidentally, a certain probability distribution is assumed in each of FIGS. 6A and 6B, and the vertical axes show relative values.

As shown in FIG. 6A, the energy Ek and El of characteristic X-rays does not appear on the incident pixel P[C3]. As shown in FIG. 6B, on the other hand, the energy Ek and El of the characteristic X-rays and difference energy Ek−El between them appears on the non-incident pixel P. Incidentally, the values of the energy Ein of the incident X-rays, the energy Ek and El of the characteristic X-rays and probabilities that the respective phenomena occur with are suitably set in the examples shown in FIGS. 6A and 6B, and something similar occurs on the practical semiconductor cell S.

FIG. 7 is a diagram showing an example of energy absorbed by the photon counting type image detector 26 in a case where X-ray photons arrive at a certain pixel P included in the photon counting type image detector 26 according to the present embodiment.

FIG. 7 shows energy absorbed by the photon counting type image detector 26 in a case where X-ray photons of the energy Ein as many as a positive integer M arrive at the pixel P[C3]. On the incident pixel P[C3], the energy Ein, Ein−Ek and Ein−Ek+El is detected m1 (ml<=M) times, m2 (m2<=M) times and m3 (m3<=M) times, respectively. Thus, a resultant counted value M on the incident pixel P[C3] is M=(m1+m2+m3). Even if the values m1, m2, and m3 change owing to that the characteristic X-rays are absorbed by the non-incident pixels Ps or emitted to the outside of the detecting membrane as being subject to probabilities, the resultant counted value M on the incident pixel P[C3], the sum of m1, m2 and m3, is not affected by the change. Although an X-ray photon which does not interact with the semiconductor cell S at all and passes through is not counted, the resultant counted value M is hardly affected by the probabilities as described above, as it is supposed that the semiconductor cell S is thick enough and that substantially 100 percent of the incident X-ray photons perform interaction to give energy into the semiconductor cell S in the photon counting type image detector 26 as described above.

The plural comparators $53_1$-$53_n$ in each of the pixels Ps in the photon counting type image detector 26 shown in FIG. 2 discriminate the energy Ek and El of the characteristic X-rays produced by the non-incident pixel P, the difference energy Ek−El and energy excepting the above absorbed by the incident pixel P (incident energy Ein and difference energy Ein−Ek and Ein−Ek+El) from one another (n>=4). The threshold logic circuit 55 does not transmit a clock pulse based on the characteristic X-ray energy Ek and El and the difference energy Ek-El to the counters $56_1$-$56_m$, resulting in that the counters $56_1$-$56_m$ does not count the characteristic X-ray energy Ek and El and the difference energy Ek−El. Thus, the photon counting type image detector 26 can remove a signal based on X-rays which leak from the incident pixel P.

Further, as the photon counting type image detector 26 can count the number of X-ray photons absorbed by the pixel P without omission by counting one event as one unit regardless of which of the energy excepting the characteristic X-ray energy Ek and El, the photon counting type image detector 26 can know the number of the X-ray photons without noise.

(First Modification)

Depending upon incident X-ray energy to be used by an X-ray diagnosis apparatus and X-ray detecting material forming the semiconductor cell S, which one of the difference between the incident X-ray energy and the characteristic X-ray energy, the characteristic X-ray energy and the incident X-ray energy is lower or higher than another one is sometimes indicated by an inequality (1) shown below. According to the photon counting type image detector 26 described above, in that case, the comparators 53₁-53ₙ, etc., need to be formed by multiple stages so as to count none of the energy Ek and El of the characteristic X-rays, which can be put into practice as follows although the circuit in the photon counting type image detector 26 is scaled up.

[Expression 1]

$$(\text{Incident X-ray energy}) - (\text{characteristic X-ray energy}) < (\text{characteristic X-ray energy}) < (\text{incident X-ray energy}) \quad (1)$$

Figure 8:
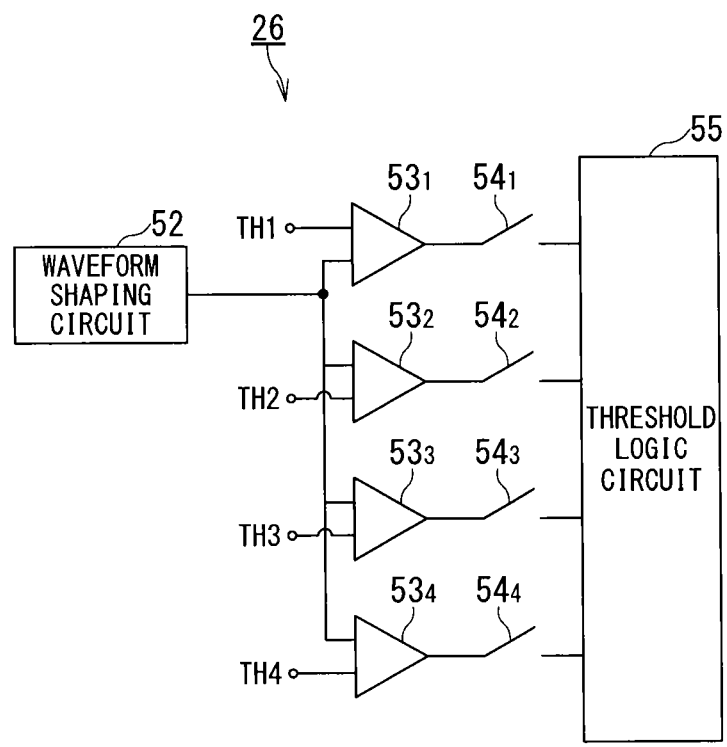
FIG. 8 is an electric block diagram centered on comparators in a first modification of the photon counting type image detector according to the present embodiment.

FIG. 8 is an electric block diagram centered on the comparators 53₁-53ₙ in a first modification of the photon counting type image detector 26 according to the present embodiment.

Let n=4 in each of the processing circuits C shown in FIG. 2 in the first modification of the photon counting type image detector 26 shown in FIG. 8. That is, the processing circuits C each have a charge amplifier 51, a waveform shaping circuit 52, comparators 53₁-53₄ of four stages, a threshold logic circuit 55 and counters 56₁-56₄ of four stages in the first modification of the photon counting type image detector 26.

In the first modification of the photon counting type image detector 26, reference values TH1 (upper limit reference value THH), TH2, TH3 and TH4 (lower limit reference value THL) are applied to reference input ends of the comparators 53₁, 53₂, 53₃ and 53₄, respectively. The reference values TH1, TH2, TH3 and TH4 are each set here according to an inequality (2) shown below.

[Expression 2]

$$TH4 < (\text{incident X-ray energy}) - (\text{characteristic X-ray energy}) < TH3 < (\text{characteristic X-ray energy}) < TH2 < (\text{incident X-ray energy}) < TH1 \quad (2)$$

FIG. 9 is a diagram illustrating logical operation for counting none of the characteristic X-ray energy Ek and El by using the comparators of four stages 53₁-53₄.

Upon obtaining a pulse signal from the comparator 53₄ and not from any one of the comparators 53₃, 53₂ and 53₁, the threshold logic circuit 55 decides that the absorbed energy is (incident X-ray energy)-(characteristic X-ray energy) as shown in FIG. 9. Upon obtaining a pulse signal from the comparator 53₃ and not from any one of the comparators 53₂ and 53₁, the threshold logic circuit 55 decides that the absorbed energy is the characteristic X-ray energy. Upon obtaining a pulse signal from the comparator 53₂ and not from the comparator 53₁, the threshold logic circuit 55 decides that the absorbed energy is the incident X-ray energy.

As being able to identify characteristic X-ray energy, the threshold logic circuit 55 explained with reference to FIG. 9 provides the counters 56₁-56ₘ with no clock pulse upon deciding that the absorbed energy is characteristic X-ray energy, so that a configuration to count none of the characteristic X-ray energy by means of the comparators 53₁-53₄ of four stages can be put into practice.

(Second Modification)

According to the photon counting type image detector 26 described above, the comparators 53₁-53ₙ, etc., need to be formed by multiple stages in order that none of the characteristic X-ray energy Ek and El is counted, resulting in that the circuit in the photon counting type image detector 26 is scaled up. If the X-ray energy to be used in the X-ray diagnosis apparatus and the X-ray detecting material forming the semiconductor cell S is suitably selected in such a way that which one of the difference between the incident X-ray energy and the characteristic X-ray energy, the characteristic X-ray energy and the incident X-ray energy is lower or higher than another one is indicated by an inequality (3) shown below, the circuit can be scaled down. Incidentally, the inequality (3) indicates a threshold margin (en) that a voltage depending upon circuit noise is converted into in X-ray energy, and the threshold margin (en) may be small if the circuit noise is small.

[Expression 3]

$$(\text{Incident X-ray energy}) - (\text{characteristic X-ray energy}) > (\text{characteristic X-ray energy}) + \text{threshold margin (en)} \quad (3)$$

The relationship indicated by the inequality (3) can be modified into an inequality (4) shown below.

[Expression 4]

$$(\text{Incident X-ray energy}) > 2 \times (\text{characteristic X-ray energy}) + \text{threshold margin (en)} \quad (b\,4)$$

Further, think of only energy of characteristic X-rays produced by the incident X-rays as the characteristic X-ray energy here. In order that characteristic X-rays, e.g., K X-ray is produced, the incident X-ray energy needs to be higher than the K absorption edge. If the incident X-ray energy is practically limited within a range lower than the K absorption edge, not K X-ray but L X-ray and M X-ray are considered. That is, as X-rays of a continuous spectrum are used for an X-ray diagnosis apparatus such as the mammography apparatus 1, and an X-ray CT apparatus having the photon counting type image detector 26, K X-ray need not be considered if upper limit energy in the X-ray spectrum is limited within the range lower than the K absorption edge.

Figure 10:
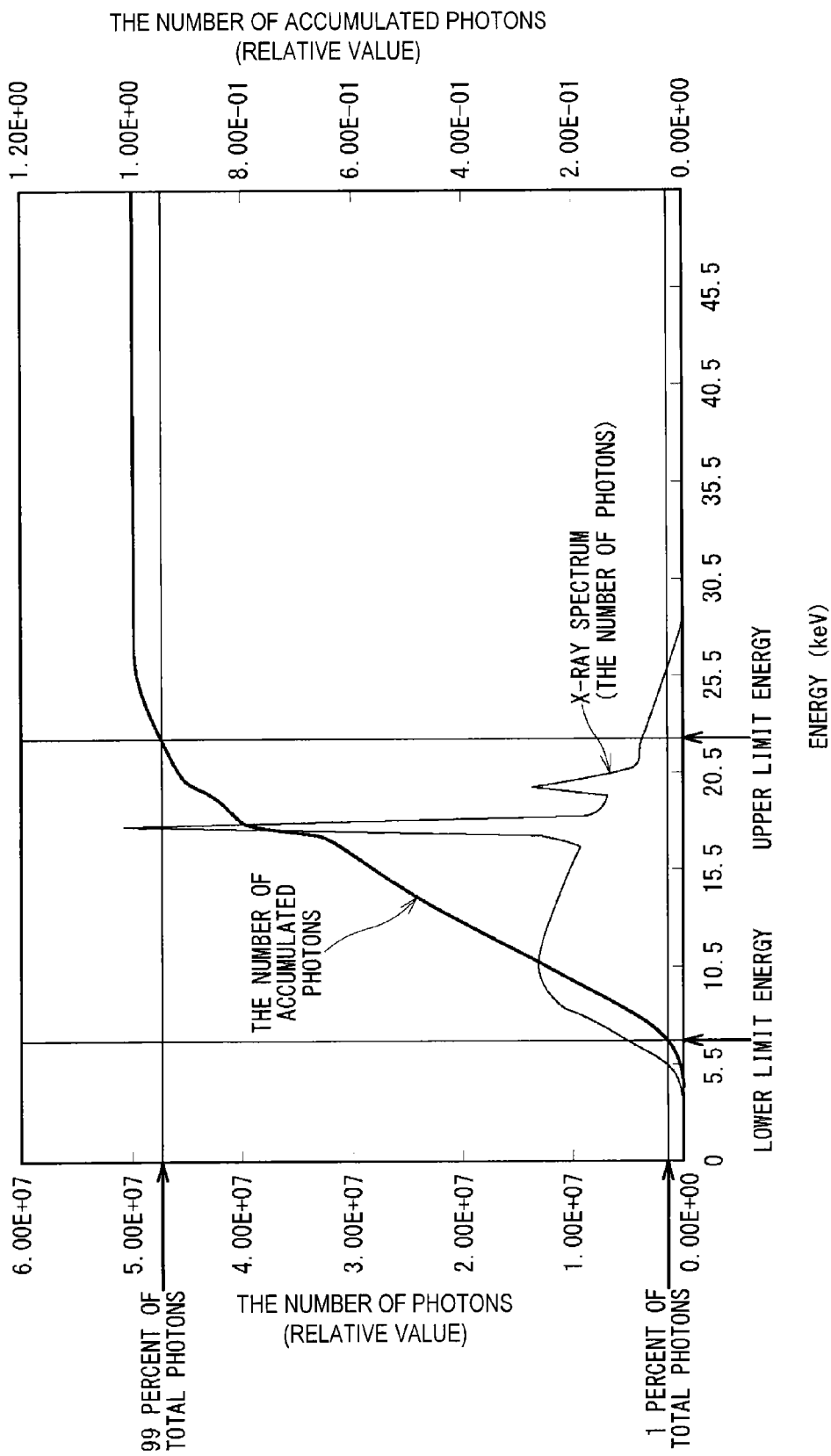
FIG. 10 is a diagram showing a graph of a continuous X-ray spectrum and the number of accumulated photons to be used in an X-ray diagnosis apparatus and an X-ray CT apparatus.

FIG. 10 is a diagram showing a graph of a continuous X-ray spectrum and the number of accumulated photons to be used in the X-ray diagnosis apparatus and the X-ray CT apparatus. FIG. 10 shows exemplary upper and lower limit energy in the X-ray spectrum of the incident X-rays.

FIG. 10 shows an X-ray spectrum (the number of photons) in an energy range including the entire X-ray spectrum and the number of accumulated photons expressed as an accumulated integral curve of a certain physical quantity (e.g., energy and the number of photons, etc.). In FIG. 10, e.g., the upper limit energy in the X-ray spectrum is defined as a lower limit in an energy range corresponding to 99 percent and over of total photons. Further, the lower limit energy in the X-ray spectrum is defined as an upper limit of an energy range corresponding to one percent and less of the total photons.

The imaging control/image processing system 12 controls quality of X-rays by controlling anode material of the X-ray tube 21, tube voltage applied to the X-ray tube 21 and the X-ray beam quality adjustment filter/irradiation field limiting mask 22 in order to control the X-ray spectrum of the incident X-rays, the upper limit energy and the lower limit energy in the X-ray spectrum as shown in FIG. 10.

If the spectrum of the incident X-rays is controlled and the semiconductor cell S is suitably selected as described above, a configuration having the comparators 53₁ and 53₂ of two stages can be put into practice as shown below. The incident X-ray energy and the semiconductor cell S is suitably controlled and selected, and the reference values THH and THL are set as shown below by equations (5-1) and (5-2). Incidentally, the highest value of the incident X-ray energy (voltage) shown by the equation (5-1) is a voltage into which the highest energy in the incident X-rays is converted. Further, the value of the characteristic X-ray energy (voltage) shown by the equation (5-2) is a voltage into which the characteristic X-ray energy is converted.

[Expression 5]

Upper limit of reference value THH for comparator
$53_1$=highest incident X-ray energy (voltage) (5-1)

Lower limit of reference value THL for comparator
$53_2$=value of characteristic X-ray energy (voltage)+threshold margin (en) (5-2)

While the X-ray diagnosis apparatus such as the mammography apparatus 1, and the X-ray CT apparatus having the photon counting type image detector 26 uses X-rays of a continuous spectrum, the relationship shown by the inequality (4) is rewritten as a following inequality (6) upon being applied to a continuous spectrum case.

[Expression 6]

Lower limit energy in X-ray spectrum>2×(value of characteristic X-ray energy)+threshold margin (en) (6)

Further, the equation (5-1) can be converted into a following equation (7).

[Expression 7]

Upper limit reference value THH for comparator
$53_1$=upper limit energy in X-ray spectrum (voltage) (7)

The upper limit reference value THH for the comparator $53_1$ can be determined from the upper limit energy in the X-ray spectrum (e.g., in FIG. 10) by the use of the equation (7). Further, the lower limit reference value THL for the comparator $53_2$ can be determined on the basis of the characteristic X-ray energy by the use of the equation (5-2).

The term "characteristic X-rays" used here exactly represents a generic name given to X-rays of a plurality of energy values. That is, K X-ray, e.g., include $K\alpha_1$ (K-$L_3$)-rays, $K\alpha_2$ (K-$L_2$)-rays, $K\beta_1$(K-$M_3$)-rays, etc. Further, the characteristic X-rays include not only K X-ray but L X-ray, M X-ray, etc. As these have energy values which are different from one another, suppose that the "characteristic X-ray energy" in the inequality (6) means "highest energy in the characteristic X-rays produced by the incident X-rays" according to the gist according to the present embodiment.

Further, as absorption edge energy of an element is slightly higher than the "highest energy in the characteristic X-rays", a similar effect can be practically obtained by the use of a next inequality (8).

[Expression 8]

Lower limit energy in X-ray spectrum>2×(absorption edge energy)+threshold margin (en) (8)

A second modification of the photon counting type image detector 26 according to the present embodiment will be explained by the use of FIGS. 11A, 11B, 12A and 12B.

Figure 11B:
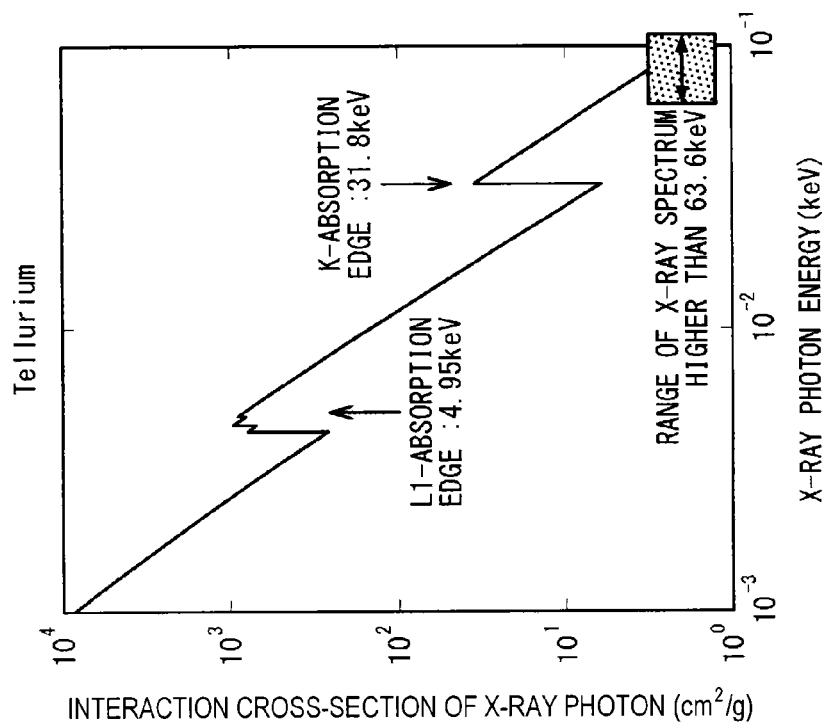
FIGS. 11A and 11B are diagrams each showing a graph of photon cross section by photoelectric effect and a range of an X-ray spectrum in a case where CdTe is used as a semiconductor cell in a chest X-ray energy region.
Figure 11A:
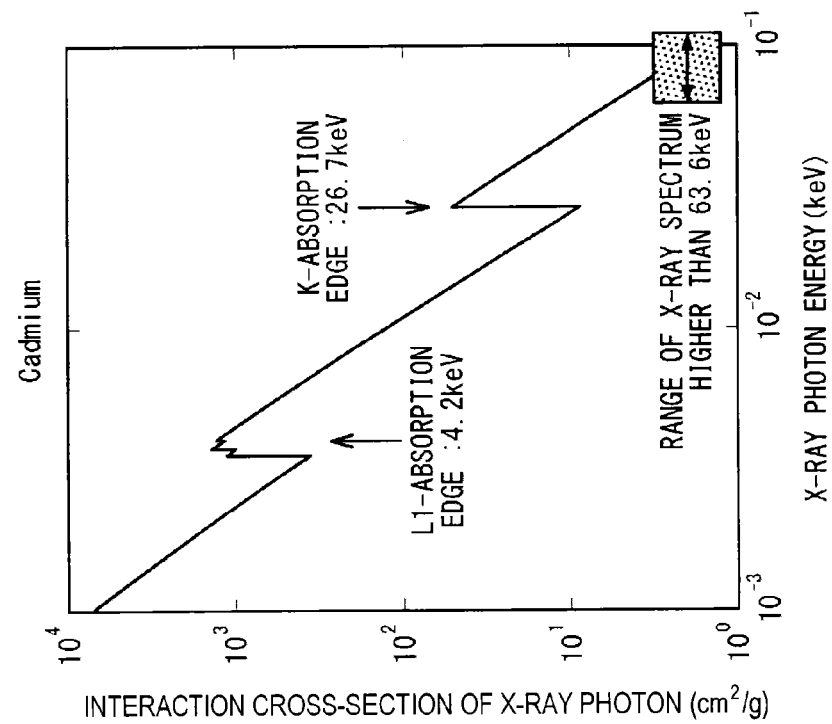

FIGS. 11A and 11B are diagrams each showing a graph of photon cross section by photoelectric effect and a range of an X-ray spectrum in a case where a compound semiconductor, e.g., CdTe is used as the semiconductor cell S in a chest X-ray energy region (approximately 50 keV and over). FIG. 11A illustrates a photoelectric effect of Cd (Cadmium) and a range of an X-ray spectrum on a graph. FIG. 11B illustrates a photoelectric effect of Te (Tellurium) and a range of an X-ray spectrum on a graph. Incidentally, as the semiconductor cell S, the compound semiconductor may be CdZnTe, etc., formed by three kinds of elements as well as CdTe formed by two kinds of elements.

In case of the chest X-ray energy region, the K-absorption edge energy of Cd relates to the K-absorption edge energy of Te as shown by a following inequality (9) on the basis of the graphs shown in FIGS. 11A and 11B. Thus, the imaging control/image processing system 12 controls quality of X-rays on the basis of the inequality (8) so that the lower limit energy in the X-ray spectrum of the incident X-rays is higher than 63.6 keV, i.e., double the K-absorption edge energy of Te having highest K-absorption edge energy in Cd and Te.

[Expression 9]

K-absorption edge of Cd=26.7 keV<K-absorption edge of Te=31.8 keV (b 9)

Suppose here that a single element such as Se, etc., is used as the semiconductor cell S. In that case, the imaging control/image processing system 12 controls the quality of X-rays merely in such a way that the lower limit energy in the X-ray spectrum of the incident X-rays is higher than double the K-absorption edge energy of the single element.

Figure 12B:
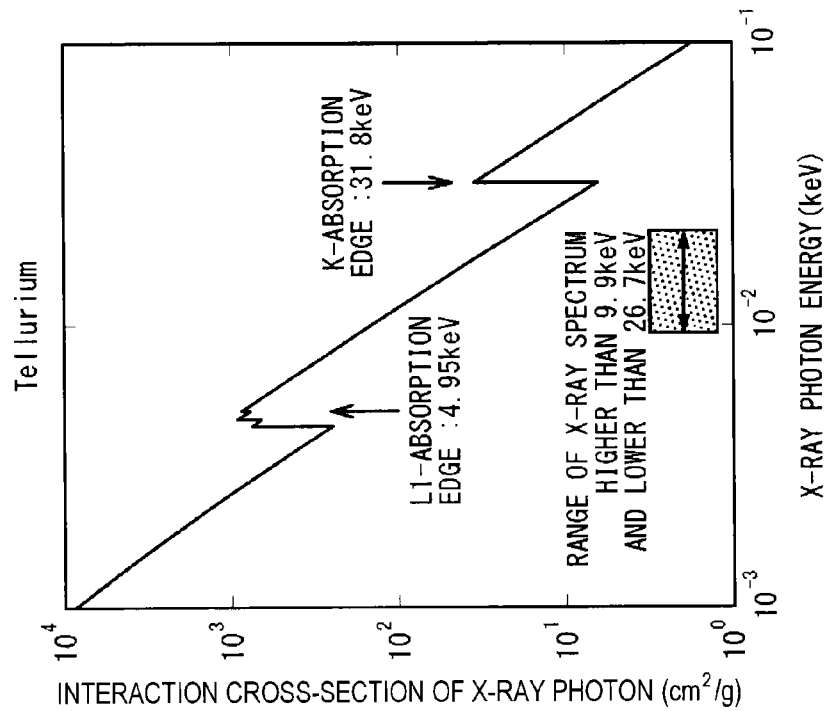
FIGS. 12A and 12B are diagrams each showing a graph of photon cross section by photoelectric effect and a range of an X-ray spectrum in a case where CdTe is used as a semiconductor cell in a mammographic X-ray energy region.
Figure 12A:
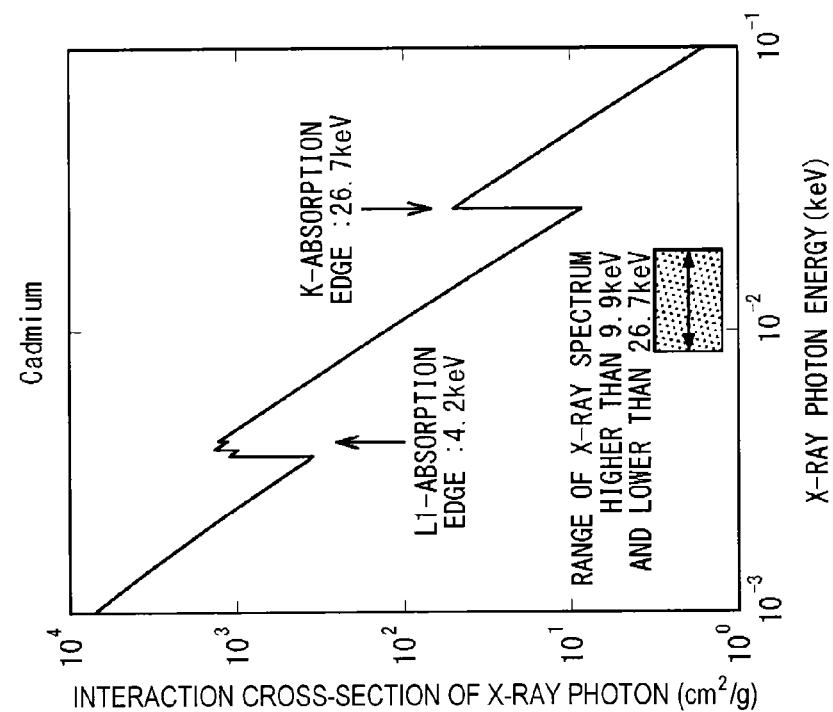

FIGS. 12A and 12B are diagrams each showing a graph of photon cross section by photoelectric effect and a range of an X-ray spectrum in a case where a compound semiconductor, e.g., CdTe is used as the semiconductor cell S in a mammographic X-ray energy region (approximately 10 keV and over). FIG. 12A illustrates a photoelectric effect of Cd and a range of an X-ray spectrum on a graph. FIG. 12B illustrates a photoelectric effect of Te and a range of an X-ray spectrum on a graph.

In case of the mammographic X-ray energy region, K-absorption edge energy of Cd relates to K-absorption edge energy of Te as shown by a following inequality (10-1) on the basis of the graphs shown in FIGS. 12A and 12B. Thus, the imaging control/image processing system 12 controls quality of X-rays so that the upper limit energy in the X-ray spectrum of the incident X-rays is lower than 26.7 keV, i.e., the K-absorption edge energy of Cd having lowest K-absorption edge energy in Cd and Te. Further, in case of the mammographic X-ray energy region, L1-absorption edge energy of Cd relates to L1-absorption edge energy of Te as shown by a following inequality (10-2) on the basis of the graphs shown in FIGS. 12A and 12B. Thus, the imaging control/image processing system 12 controls quality of X-rays so that the lower limit energy in the X-ray spectrum of the incident X-rays is higher than 9.9 keV, i.e., double the L1-absorption edge energy of Te having highest L1-absorption edge energy in Cd and Te.

[Expression 10]

K-absorption edge of Cd=26.7 keV<K-absorption edge of Te=31.8 keV (b 10-1)

L1-absorption edge of Cd=4.2 keV<L1-absorption edge of Te=4.95 keV (10-2)

Suppose here that a single element such as Se, etc., is used as the semiconductor cell S. In that case, the imaging control/image processing system 12 controls the quality of X-rays merely in such a way that the upper limit energy in the X-ray spectrum of the incident X-rays is lower than the K-absorption edge energy of the single element. Further, the imaging control/image processing system 12 controls the quality of X-rays simply in such a way that the lower limit energy in the X-ray spectrum of the incident X-rays is higher than double the L1-absorption edge energy of the single element.

Incidentally, an exemplary operation to be done by the imaging control/image processing system 12 for controlling the upper limit energy in the X-ray spectrum will be specifically explained. Let the tube voltage of the X-ray tube 21 be Etube[kV], and then the X-ray spectrum of the incident X-rays is limited to Etube[kV] and below. Further, if a beam filter including a particular element is installed close to a radiation aperture of the X-ray tube 21 as another method, X-ray absorption with energy slightly higher than the K-absorption edge Ek_bmflt of the element grows and the upper limit of the spectrum can thereby be controlled owing to selection of an element for which Ek_bmflt corresponds to a higher energy side in the X-ray spectrum.

Further, an exemplary operation to be done by the imaging control/image processing system 12 for controlling the lower limit energy in the X-ray spectrum will be specifically explained. An element having a K-absorption edge which is lower than an energy range to be used for production of an X-ray image (light element) is used as a beam filter. In that case, the absorption grows as the energy turns lower, and the lower limit energy in the X-ray spectrum is controlled by the use of it.

As the photon counting type image detector 26 according to the present embodiment, or the X-ray diagnosis apparatus or the X-ray CT apparatus having the photon counting type image detector 26 can reduce an expanse of a signal in the detector, an X-ray image of high resolution can be provided. Further, as being a stochastic phenomenon, the signal expanse is reduced so that image noise can be reduced in an X-ray image.

Further, according to a modification of the photon counting type image detector 26 according to the present embodiment, or the X-ray diagnosis apparatus or the X-ray CT apparatus having the modification of the photon counting type image detector 26, an X-ray image of high resolution can be provided without the use of a complicated (having multiple stages) circuit structure.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A photon counting type image detector comprising:
    an X-ray detecting material configured to detect an X-ray photon;
    a charge-to-voltage converter configured to generate a plurality of electric pulses each being based on an electric charge collected in response to the detected X-ray photon;
    an energy discriminator configured to discriminate a peak value of each of the electric pulses;
    a controller configured to perform control so as not to count a non-count pulse of the peak-discriminated electric pulses, the non-count pulse corresponding to energy of characteristic X-rays produced in the X-ray detecting material; and
    a counter configured to count a count pulse of the peak-discriminated electric pulses, the count pulse being obtained by removing the non-count pulse from the peak-discriminated electric pulses.

2. An X-ray diagnosis apparatus having the photon counting type image detector according to claim 1.

3. The X-ray diagnosis apparatus according to claim 2, wherein
    the controller performs control so as not to count the non-count pulses of the peak-discriminated electric pulses, the non-count pulses corresponding to the characteristic X-ray energy and corresponding to a difference between plural different energy values of characteristic X-rays produced in the X-ray detecting material.

4. The X-ray diagnosis apparatus according to claim 2, further comprising:
    an X-ray beam quality controller configured to control quality of the X-rays by controlling material of an anode of an X-ray tube, tube voltage to be applied to the X-ray tube and a quality filter put in front of the X-ray tube, wherein
    the quality controller controls quality of the X-rays in such a way that lower limit energy in an X-ray spectrum of the X-rays is over double characteristic X-ray energy of the X-ray detecting material.

5. The X-ray diagnosis apparatus according to claim 2, further comprising:
    an X-ray beam quality controller configured to control quality of the X-rays by controlling material of an anode of an X-ray tube, tube voltage to be applied to the X-ray tube and a quality filter put in front of the X-ray tube, wherein
    the quality controller controls quality of the X-rays, upon the X-ray detecting material being formed by a plurality of elements, in such a way that lower limit energy in an X-ray spectrum of the X-rays is over double a highest value of characteristic X-ray energy of the plural elements.

6. The X-ray diagnosis apparatus according to claim 2, further comprising:
    an X-ray beam quality controller configured to control quality of the X-rays by controlling material of an anode of an X-ray tube, tube voltage to be applied to the X-ray tube and a quality filter put in front of the X-ray tube, wherein
    the quality controller controls quality of the X-rays, upon the characteristic X-ray energy including first characteristic X-ray energy and second characteristic X-ray energy which is lower than the first characteristic energy and no other characteristic X-ray energy being between the first characteristic X-ray energy and the second characteristic X-ray energy, in such a way that lower limit energy in an X-ray spectrum of the X-rays is over double the second characteristic X-ray energy and that upper limit energy in the X-ray spectrum equals the first characteristic X-ray energy and below.

7. The X-ray diagnosis apparatus according to claim 2, further comprising:
    an X-ray beam quality controller configured to control quality of the X-rays by controlling material of an anode of an X-ray tube, tube voltage to be applied to the X-ray tube and a quality filter put in front of the X-ray tube, wherein
    the quality controller controls quality of the X-rays, upon the X-ray detecting material being formed by a plurality of elements, the characteristic X-ray energy including first characteristic X-ray energy and second characteristic X-ray energy which is lower than the first characteristic energy and no other characteristic X-ray energy being between the first characteristic X-ray energy and the second characteristic X-ray energy, in such a way that lower limit energy in an X-ray spectrum of the X-rays is over double a highest value of the second characteristic X-ray energy of the plural elements and that upper limit energy in the X-ray spectrum equals a lowest value of the first characteristic X-ray energy of the plural elements and below.

8. An X-ray computed tomography apparatus having the photon counting type image detector according to claim 1.

9. The X-ray computed tomography apparatus according to claim 8, wherein the controller performs control so as not to count the non-count pulses of the peak-discriminated electric pulses, the non-count pulses corresponding to the characteristic X-ray energy and corresponding to a difference between plural different energy values of characteristic X-rays produced in the X-ray detecting material.

10. The X-ray computed tomography apparatus according to claim 8, further comprising:
an X-ray beam quality controller configured to control quality of the X-rays by controlling material of an anode of an X-ray tube, tube voltage to be applied to the X-ray tube and a quality filter put in front of the X-ray tube, wherein
the quality controller controls quality of the X-rays in such a way that lower limit energy in an X-ray spectrum of the X-rays is over double characteristic X-ray energy of the X-ray detecting material.

11. The X-ray computed tomography apparatus according to claim 8, further comprising:
an X-ray beam quality controller configured to control quality of the X-rays by controlling material of an anode of an X-ray tube, tube voltage to be applied to the X-ray tube and a quality filter put in front of the X-ray tube, wherein
the quality controller controls quality of the X-rays, upon the X-ray detecting material being formed by a plurality of elements, in such a way that lower limit energy in an X-ray spectrum of the X-rays is over double a highest value of characteristic X-ray energy of the plural elements.

12. The X-ray computed tomography apparatus according to claim 8, further comprising:
an X-ray beam quality controller configured to control quality of the X-rays by controlling material of an anode of an X-ray tube, tube voltage to be applied to the X-ray tube and a quality filter put in front of the X-ray tube, wherein
the quality controller controls quality of the X-rays, upon the characteristic X-ray energy including first characteristic X-ray energy and second characteristic X-ray energy which is lower than the first characteristic energy and no other characteristic X-ray energy being between the first characteristic X-ray energy and the second characteristic X-ray energy, in such a way that lower limit energy in an X-ray spectrum of the X-rays is over double the second characteristic X-ray energy and that upper limit energy in the X-ray spectrum equals the first characteristic X-ray energy and below.

13. The X-ray computed tomography apparatus according to claim 8, further comprising:
an X-ray beam quality controller configured to control quality of the X-rays by controlling material of an anode of an X-ray tube, tube voltage to be applied to the X-ray tube and a quality filter put in front of the X-ray tube, wherein
the quality controller controls quality of the X-rays, upon the X-ray detecting material being formed by a plurality of elements, the characteristic X-ray energy including first characteristic X-ray energy and second characteristic X-ray energy which is lower than the first characteristic energy and no other characteristic X-ray energy being between the first characteristic X-ray energy and the second characteristic X-ray energy, in such a way that lower limit energy in an X-ray spectrum of the X-rays is over double a highest value of the second characteristic X-ray energy of the plural elements and that upper limit energy in the X-ray spectrum equals a lowest value of the first characteristic X-ray energy of the plural elements and below.

* * * * *